(12) United States Patent
Kerr et al.

(10) Patent No.: US 8,968,359 B2
(45) Date of Patent: Mar. 3, 2015

(54) SURGICAL FORCEPS

(75) Inventors: Duane E. Kerr, Loveland, CO (US); Jeffrey R. Townsend, Loveland, CO (US)

(73) Assignee: Covidien LP, Mansfield, MA (US)

( * ) Notice: Subject to any disclaimer, the term of this patent is extended or adjusted under 35 U.S.C. 154(b) by 730 days.

(21) Appl. No.: 12/773,526

(22) Filed: May 4, 2010

(65) Prior Publication Data

US 2011/0276048 A1 Nov. 10, 2011

(51) Int. Cl.
*A61B 17/285* (2006.01)
*A61B 17/295* (2006.01)
*A61B 18/14* (2006.01)
*A61B 17/29* (2006.01)
*A61B 18/00* (2006.01)

(52) U.S. Cl.
CPC ........... *A61B 17/295* (2013.01); *A61B 18/1445* (2013.01); *A61B 2017/2929* (2013.01); *A61B 2018/00196* (2013.01); *A61B 2018/00601* (2013.01); *A61B 2018/0063* (2013.01); *A61B 2018/1412* (2013.01)
USPC .................. 606/207; 606/45; 606/51; 606/52

(58) Field of Classification Search
CPC ........... A61B 18/1442; A61B 18/1445; A61B 2017/1125; A61B 2017/28; A61B 2017/29; A61B 2017/2903; A61B 2017/291; A61B 2017/2929; A61B 2017/293; A06B 2018/1442; A06B 2018/145; A06B 2018/1452; A06B 2018/1462
USPC ...................... 606/32–52, 167–189, 205–207
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| 5,002,565 A * | 3/1991 | McGregor | 606/223 |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Ronald Hupczey, Jr.

(57) ABSTRACT

A forceps includes a housing, a shaft, and an end effector assembly. The end effector assembly includes first and second jaw members. At least one of the jaw members is moveable with respect to the other between a spaced-apart position and an approximated position for grasping tissue therebetween. A cutting member having a plurality of cutting edges symmetrically-disposed about a longitudinal axis thereof is disposed within the shaft and is longitudinally translatable between a retracted position and an extended position. The cutting member extends between the jaw members to cut tissue grasped therebetween when in the extended position. The cutting member is fixedly-oriented with respect to the shaft and is configured for translation between the jaw members to cut tissue therebetween when the jaw members are rotated with respect to the shaft between about zero degrees and about 180 degrees in at least one of the clockwise and counterclockwise directions.

7 Claims, 6 Drawing Sheets

(56) References Cited

U.S. PATENT DOCUMENTS

| | | | |
|---|---|---|---|
| 5,171,250 A | 12/1992 | Yoon | |
| 5,176,695 A * | 1/1993 | Dulebohn | 606/170 |
| 5,217,477 A * | 6/1993 | Lager | 606/167 |
| 5,318,589 A * | 6/1994 | Lichtman | 606/205 |
| D348,930 S | 7/1994 | Olson | |
| 5,342,389 A * | 8/1994 | Haber et al. | 606/205 |
| 5,458,598 A * | 10/1995 | Feinberg et al. | 606/52 |
| 5,554,164 A | 9/1996 | Wilson et al. | |
| D384,413 S | 9/1997 | Zlock et al. | |
| 5,665,100 A * | 9/1997 | Yoon | 606/170 |
| 5,797,938 A | 8/1998 | Paraschac et al. | |
| 5,797,941 A * | 8/1998 | Schulze et al. | 606/171 |
| 5,894,939 A * | 4/1999 | Frankel | 209/630 |
| 5,984,939 A * | 11/1999 | Yoon | 606/170 |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D493,888 S | 8/2004 | Reschke | |
| 6,773,434 B2 * | 8/2004 | Ciarrocca | 606/51 |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,465,310 B2 * | 12/2008 | Isogimi | 606/167 |
| 7,481,810 B2 * | 1/2009 | Dumbauld et al. | 606/51 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,142,474 B2 * | 3/2012 | Hafner | 606/207 |
| 2004/0106948 A1 * | 6/2004 | Cunningham | 606/223 |
| 2008/0021450 A1 | 1/2008 | Couture | |
| 2009/0125026 A1 * | 5/2009 | Rioux et al. | 606/45 |
| 2010/0185197 A1 * | 7/2010 | Sakao et al. | 606/51 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009,
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2008.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.

(56) References Cited

OTHER PUBLICATIONS

U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.

(56) References Cited

OTHER PUBLICATIONS

Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Intl Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

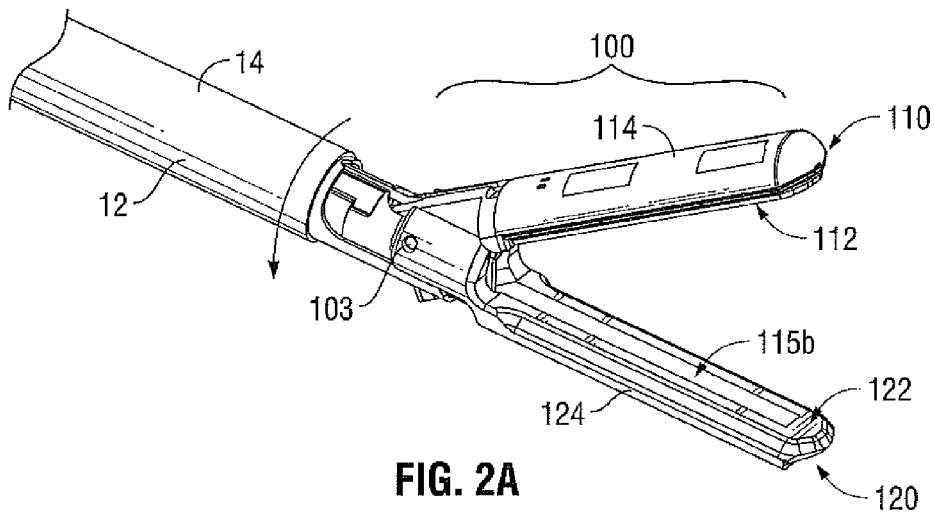
FIG. 2A
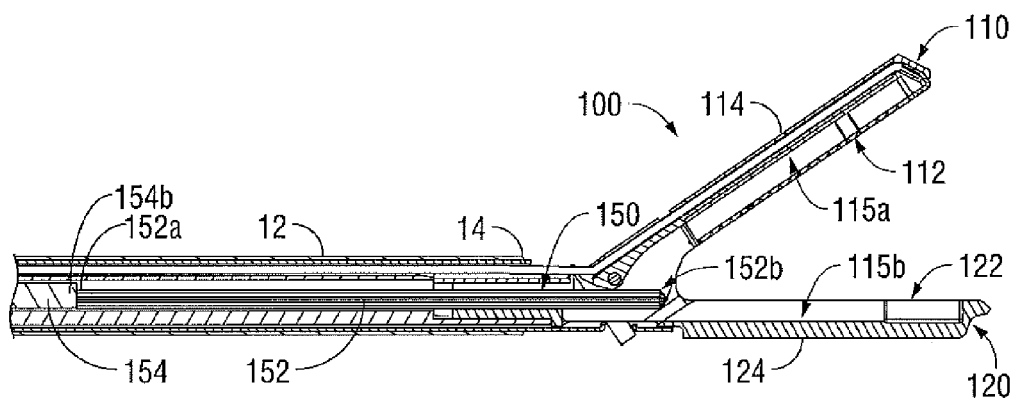
FIG. 2B
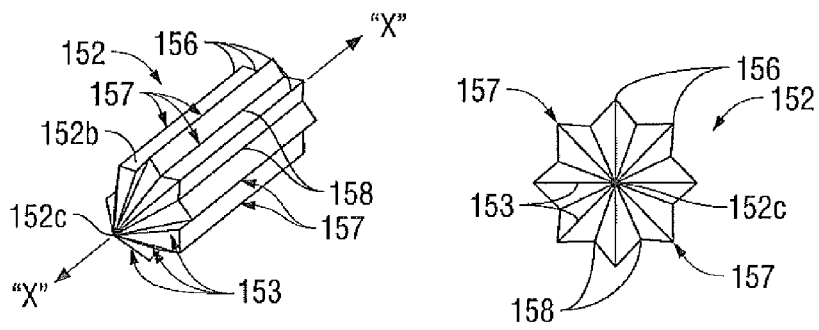
FIG. 3A  FIG. 3B

SURGICAL FORCEPS

BACKGROUND

The present disclosure relates to surgical instruments. More particularly, the present disclosure relates to surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps. The forceps includes a housing having a shaft attached thereto and an end effector assembly disposed at a distal end of the shaft. The end effector assembly includes first and second jaw members disposed in opposed relation relative to one another. One (or both) of the jaw members is moveable with respect to the other between a spaced-apart position and an approximated position for grasping tissue therebetween. A cutting assembly is disposed within the shaft and is fixedly-oriented with respect to the shaft. The cutting assembly includes a cutting member having a plurality of cutting edges symmetrically-disposed about a longitudinal axis thereof. The cutting member is longitudinally translatable between a retracted position and an extended position. The cutting member extends between the jaw members to cut tissue grasped between the jaw members when in the extended position and is translatable to the extended position when the jaw members are rotated with respect to the shaft between about zero degrees and about 180 degrees in the clockwise and/or counterclockwise directions.

In one embodiment, the cutting member defines a starburst front cross-sectional configuration. The cutting member may also include a conically shaped distal end. The conically shaped distal end extends distally from and radially inwardly with respect to the cutting member to form a distal tip thereof.

In another embodiment, a channel is defined within and extends longitudinally along one (or both) of the jaw members. The channel(s) is configured for translation of the cutting member therethrough when the cutting member is translated from the retracted position to the extended position.

In yet another embodiment, a rotating assembly is disposed within the housing. The rotating assembly is operably coupled to the end effector assembly. More specifically, the rotating assembly is configured to rotate with respect to the shaft to rotate the end effector assembly with respect to the shaft about a longitudinal axis thereof between about zero degrees and about 180 degrees in at least one of the clockwise and counterclockwise directions.

The present disclosure also relates to a forceps including a housing having a shaft attached thereto and an end effector assembly disposed at a distal end of the shaft. The end effector assembly includes first and second jaw members disposed in opposed relation relative to one another. One (or both) jaw members is moveable with respect to the other between a spaced-apart position and an approximated position for grasping tissue therebetween. A cutting assembly including a cutting member is disposed within the shaft. The cutting member defines a diamond-shaped front cross-sectional configuration and includes four cutting edges extending longitudinally therealong. The cutting member is longitudinally translatable between a retracted position and an extended position. In the extended position, the cutting member extends between the jaw members to cut tissue disposed therebetween.

In one embodiment, one (or both) of the jaw members includes a channel defined therein and extending longitudinally therealong. The channel(s) is shaped complementarily, or quasi-complementarily, to the cutting member and is configured to permit translation of the cutting member therethrough when the cutting member is translated to the extended position.

In another embodiment, the cutting member defines another cutting edge at a distal end thereof.

In accordance with another embodiment of the present disclosure, a forceps is provided. As in the previous embodiments, the forceps includes a housing having a shaft attached thereto. The shaft defines a longitudinal axis and has an end effector assembly disposed at a distal end thereof. The end effector assembly includes first and second jaw members disposed in opposed relation relative to one another. One (or both) of the jaw members is moveable with respect to the other between a spaced-apart position and an approximated position for grasping tissue therebetween. One (or both) of the jaw members includes an electrically conductive tissue sealing surface disposed on an opposed surface thereof. A cutting assembly including a cutting member is disposed within the shaft. The cutting member defines a rectangular front cross-sectional configuration. The cutting member is longitudinally translatable between a retracted position and an extended position. When translated to the extended position, the cutting member extends between the jaw members in a substantially parallel orientation with respect to the sealing surface(s) of the jaw members to cut tissue disposed therebetween.

In accordance with yet another embodiment of the present disclosure, a forceps is provided. The forceps includes a housing having a shaft attached thereto and an end effector assembly disposed at a distal end of the shaft. The end effector assembly includes first and second jaw members disposed in opposed relation relative to one another. One (or both) of the jaw members is moveable with respect to the other between a spaced-apart position and an approximated position for grasping tissue therebetween. One (or both) of the jaw members includes a channel defined therein and extending longitudinally therealong. The channel includes a repeating wave-shaped bottom surface. A cutting member is positioned within the channel and includes a complementary repeating wave-shaped bottom cutting surface. The cutting member is longitudinally translatable with respect to the channel. Upon longitudinal translation of the cutting member with respect to the channel, the cutting member is vertically displaced between a first position and a second position. In the first position, the bottom cutting surface of the cutting member is out of phase with the bottom surface of the channel. In the second position, the bottom cutting surface of the cutting member is in phase with the bottom surface of the channel such that the cutting member is vertically displaced from the channel to expose the bottom cutting surface for cutting tissue disposed between the jaw members.

In one embodiment, the bottom surface of the channel defines a sine wave-shaped configuration. The bottom cutting surface of the cutting member may also define a sine wave-shaped configuration.

In another embodiment, when the cutting member is in the first position, the bottom cutting surface is unexposed.

BRIEF DESCRIPTION OF THE DRAWINGS

Various embodiments of the presently disclosed forceps are described herein with reference to the drawings, wherein:

FIG. 2A is an enlarged, perspective view of one embodiment of an end effector assembly for use with the forceps of FIG. 1;

FIG. 2B is a side, cross-sectional view of the end effector assembly of FIG. 2A;

FIG. 3A is a perspective view of a cutting member configured for translation between jaw members of the end effector assembly of FIG. 2A;

FIG. 3B is a front view of the cutting member of FIG. 3A;

DETAILED DESCRIPTION

Figure 1:
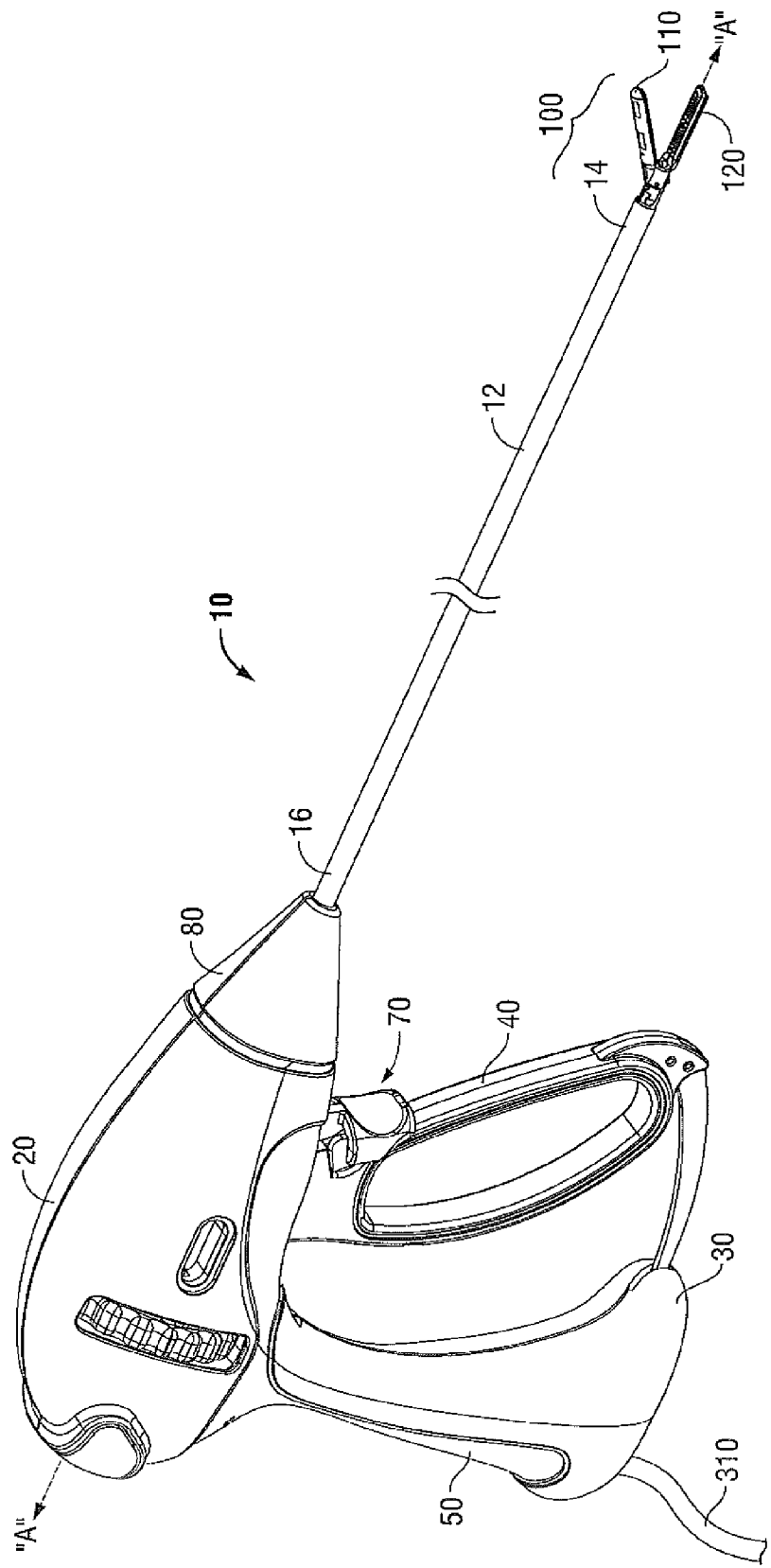
FIG. 1 is a perspective view of a forceps in accordance with the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Housing 20 includes two halves that house the internal working components of forceps 10.

End effector assembly 100 includes a pair of opposed jaw members 110 and 120. End effector assembly 100 is designed as a unilateral assembly, i.e., jaw member 120 is fixed relative to shaft 12 and jaw member 110 is moveable about a pivot 103 (FIG. 2) relative to jaw member 120. However, either, or both jaw members 110, 120 may be moveable with respect to the other.

Forceps 10 also includes an electrosurgical cable 310 that connects forceps 10 to a generator (not shown). Cable 310 has sufficient length to extend through shaft 12 in order to provide electrical energy to at least one of jaw members 110 and 120 of end effector assembly 100.

With continued reference to FIG. 1, handle assembly 30 includes a fixed handle 50 and a moveable handle 40. Fixed handle 50 is integrally associated with housing 20 and moveable handle 40 is moveable relative to fixed handle 50. Moveable handle 40 of handle assembly 30 is ultimately connected to a drive assembly (not shown) that, together, mechanically cooperate to impart movement of jaw members 110 and 120 between an open, or spaced-apart position and a closed, or approximated position.

Rotating assembly 80 is integrally associated with housing 20 and is rotatable approximately 180 degrees in either direction about a longitudinal axis "A-A" to rotate end effector assembly 100 and, thus, jaw members 110, 120, with respect to housing 20 about longitudinal axis "A-A."

Although forceps 10 is illustrated in FIG. 1 as being a laparoscopic surgical instrument, the teachings of the present disclosure may also be applicable to open surgical instruments.

Referring now to FIGS. 2A-5B, one embodiment of an end effector assembly and corresponding cutting assembly are shown generally identified by reference numerals 100 and 150, respectively. With reference initially to FIG. 2A, each jaw member 110, 120 of end effector assembly 100 includes an electrically conductive tissue sealing surface 112, 122, respectively, disposed on an opposed surface thereof and a respective outer jaw housing 114, 124. A channel 115b is defined within jaw member 120 extending longitudinally therealong. Channel 115b bisects sealing surface 122 and, as will be discussed in greater detail below, is configured for translation of a cutting member, e.g., cutting member 152 (FIGS. 3A-3B), therethrough. A complementary channel 115a (FIG. 4) may be defined within jaw member 110 such that, upon approximation of jaw members 110, 120, channel halves 115a and 115b align to form a complete channel 115. Channels 115a, 115b may define complementary half-circular cross-sections (see FIGS. 5A-5B) such that, upon approximation of jaw members 110, 120, channels 115a, 115b cooperate to form a longitudinally-extending cylindrical channel 115. Alternatively, channel 115 may define any other configuration suitable for translation of a cutting member, e.g., cutting member 152 (FIGS. 3A-3B), therethrough.

Referring now to FIG. 2B, cutting assembly 150 is disposed within shaft 12 and includes a cutting member 152 and a drive bar 154 that is coupled to trigger 70 (FIG. 1) at a proximal end thereof. Cutting member 152 is distally translatable from a retracted position, wherein cutting member 152 is disposed within shaft 12, to an extended position wherein cutting member 152 extends at least partially through channel 115 (formed by channel halves 115a, 115b) to cut tissue disposed between jaw members 110, 120 when jaw members 110, 120 are in the approximated position. More particularly, upon activation, e.g., upon depression of trigger 70 (FIG. 1), drive bar 154 is advanced distally through shaft 12. A proximal end 152a of cutting member 152 is fixedly engaged to a distal end 154b of drive bar 154 and thus, as drive bar 154 is advanced distally, cutting member 152 is similarly advanced distally through shaft 12 and into channel 115 defined by channels halves 115a, 115b of jaw members 110, 120, respectively. In other words, depressing trigger 70 (FIG. 1) translates drive bar 154 distally and drive bar 154, in turn, translates cutting member 152 distally from the retracted position to the extended position.

Cutting assembly 150 may be biased, e.g., spring biased, toward a proximal position such that cutting member 152 is biased toward the retracted position. Additionally, due to the bias of cutting assembly 150 toward the retracted position, once cutting member 152 has been deployed to the extended position, e.g., to cut tissue disposed between jaw members 110, 120, cutting member 152 would automatically return to the at-rest, or retracted position within shaft 12. Further, cutting assembly 150 and/or end effector assembly 100 may include a locking feature (not explicitly shown) for preventing deployment of cutting member 152 when jaw members 110, 120 are in the spaced-apart position.

FIGS. 3A and 3B show one embodiment of a cutting member 152 for use with cutting assembly 150. Cutting member 152 generally defines an elongated cylindrical configuration with a conically-shaped distal end 152b. Cutting member 152 may define a radially symmetrical starburst front cross-sectional configuration. More specifically, a series of alternating protrusions 156 and channels 158 may be positioned radially about a longitudinal axis "X-X" of cutting member 152, extending longitudinally therealong. Protrusions 156 and channels 158 define similarly dimensioned but oppositely disposed triangular cross-sectional configurations. A peak 157 of each protrusion 156 defines a longitudinally extending cutting edge 157, as best shown in FIG. 3A. Accordingly, with cutting edges 157 of protrusions 156 extending longitudinally along a substantial length of cutting member 152 and symmetrically positioned radially about a circumference of cutting member 152, cutting member 152 is configured to cut tissue when translated therethrough in any rotational orientation, i.e., cutting member 152 may be rotated with respect to tissue from about zero (0) degrees to about 360 degrees without affecting the cutting ability of cutting member 152 when advanced through tissue. Protrusions 156 and channels 158 extend distally and radially inwardly at distal end 152b of cutting member 152 to define conically-shaped distal end 152b. Cutting edges 153 are formed on conically shaped distal end 152b and extend distally and radially inwardly along conically shaped distal end 152b, eventually converging to form a distal tip 152c of cutting member 152. Distal tip 152c is centered on longitudinal axis "X-X" such that, as mentioned above, cutting member 152 defines a radially symmetrical configuration about longitudinal axis "X-X." As mentioned above, cutting member 152, including distal end 152b, is configured to cut tissue when translated therethrough in any rotational orientation.

Figure 4:
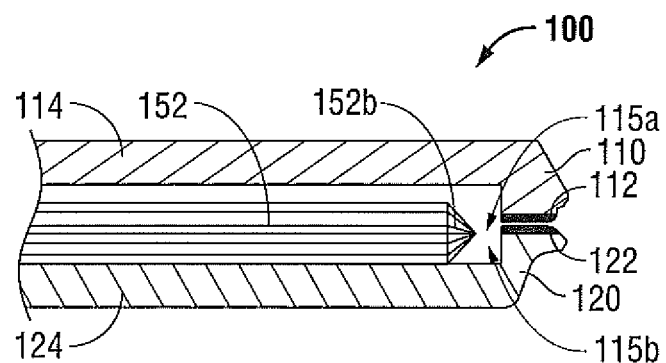
FIG. 4 is a side, cross-sectional view of the end effector assembly of FIG. 2 showing the cutting member of FIG. 3A translating therethrough.
Figure 5A:
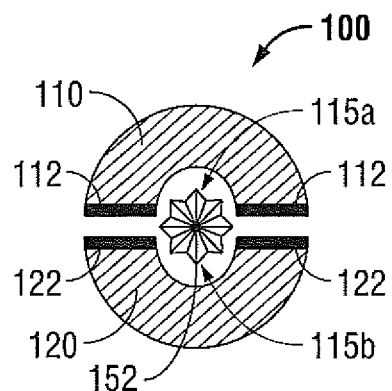
FIG. 5A is a front, cross-sectional view of the end effector assembly of FIG. 2 showing the cutting member of FIG. 3A translating therethrough.
Figure 5B:
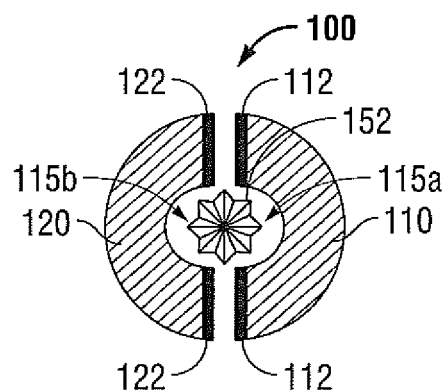
FIG. 5B is a front, cross-sectional view of the end effector assembly of FIG. 2 showing the cutting member of FIG. 3A translating therethrough and wherein the jaw members have been rotated 90 degrees from the position of FIG. 5A.

In operation, with reference now to FIGS. 4 and 5A-5B, jaw members 110, 120 are initially positioned such that tissue to be sealed and/or cut is disposed between sealing surfaces 112, 122 of jaw members 110, 120 with jaw members 110, 120 in the spaced-apart position. In order to better position jaw members 110, 120, it may be necessary to rotate rotating assembly 80. As mentioned above, rotating assembly 80 (FIG. 1) is rotatable approximately 180 degrees in either direction about longitudinal axis "A-A" of forceps 10 (FIG. 1). When rotated, rotating assembly 80 (FIG. 1) effects similar rotation of jaw member 110, 120 with respect to longitudinal axis "A-A" to better position jaw members 110, 120 about tissue.

With jaw members 110, 120 disposed about tissue, jaw members 110, 120 may be moved to the approximated position, e.g., by squeezing moveable handle 40 with respect to fixed handle 50, for grasping tissue therebetween. Electrosurgical energy may then be supplied to sealing surfaces 112 and/or 122 of jaw members 110, 120, respectively, for conducting energy through tissue grasped therebetween to effect a tissue seal.

Upon completion of tissue sealing (or once tissue has been grasped between jaw members 110, 120 in instances where only cutting is desired), cutting member 152 of cutting assembly 150 may be deployed to cut tissue grasped between jaw members 110, 120. As mentioned above, upon depression of trigger 70 (FIG. 1), drive bar 154 (FIG. 2B) is advanced distally through shaft 12 (FIG. 2B), advancing cutting member 152 distally from shaft 12. Cutting member 152 is advanced distally from shaft 12, into end effector assembly 100 and through channels 115a and 115b of jaw members 110, 120, respectively, as shown in FIG. 4, to cut tissue disposed therebetween.

Due to the radially symmetrical configuration of cutting member 152 discussed above, cutting assembly 150 need not be rotated in conjunction with jaw members 110, 120 to cut tissue therebetween. For example, as shown in FIG. 5A, cutting member 152, which may be rotationally fixed with respect to longitudinal axis "A-A" (FIG. 1), is deployable through channels 115a, 115b when jaw members are in a first rotational position with respect to longitudinal axis "A-A" (FIG. 1), e.g., where jaw members 110, 120 have not been rotated with respect to longitudinal axis "A-A" (FIG. 1). Similarly, as shown in FIG. 5B, without the need to rotate cutting member 152, cutting member 152 is deployable through channels 115a, 115b when jaw members 110, 120 are rotated to a second rotational position, e.g., wherein jaw members 110, 120 are rotated 90 degrees from the first position with respect to longitudinal axis "A-A" (FIG. 1).

Further, the configuration of cutting member 152, and more particularly, the multiple cutting edges 157 positioned radially about and extending longitudinally along cutting member 152 provide a greater cutting area, facilitating dissection of tissue as cutting member 152 is translated through tissue, regardless of the rotational orientation of cutting member 152 with respect to tissue.

Figure 6:
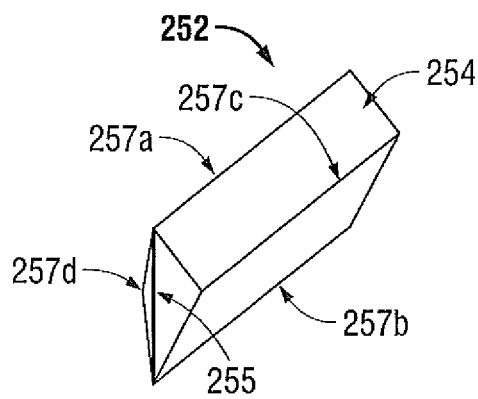
FIG. 6 is a perspective view of another cutting member in accordance with the present disclosure and configured for use with the forceps of FIG. 1.
Figure 7:
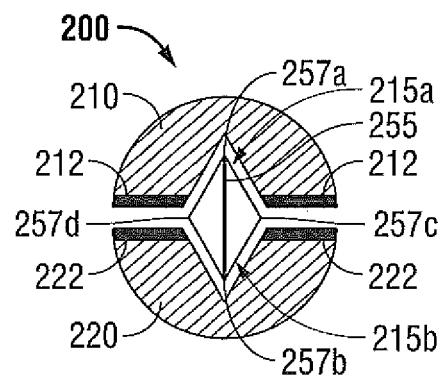
FIG. 7 is a front, cross-sectional view of an end effector assembly for use with the forceps of FIG. 1 showing the cutting member of FIG. 6 translating therethrough.

With reference now to FIGS. 6 and 7, another embodiment of a cutting member for use with forceps 10 is shown generally identified by reference numeral 252. More particularly, cutting member 252 is configured for use with an end effector assembly 200, similar to end effector assembly 100. Cutting member 252 defines an elongated body having a diamond-shaped front cross-sectional configuration. The diamond-shaped configuration of cutting member 252 forms four (4) cutting edges 257: a top cutting edge 257a, a bottom cutting edge 257b, a right cutting edge 257c, and a left cutting edge 257d. Each cutting edge 257 extends longitudinally along elongated diamond-shaped cutting member 252, as best shown in FIG. 6. Distal end 252b of cutting member 252 angles radially inward from opposed sides thereof to define a front, or distal cutting edge 255. Cutting member 252, as described above, is shaped to provide a greater surface area for cutting tissue upon translation of cutting member 252 through tissue disposed between jaw members 110, 120.

As in the previous embodiment, cutting member 252 is initially disposed within shaft 12 (FIG. 1) and is deployable therefrom from a retracted position to an extended position. Further, cutting member 252 may be fixedly engaged at a distal end thereof to a drive bar, e.g., drive bar 154 (FIG. 2B) for translating cutting member 252 between the retracted and extended positions.

As shown in FIG. 7, channels 215a, 215b of jaw members 210, 220, respectively, each define opposed triangular front cross-sectional configurations such that, upon approximation of jaw members 210, 220, channel 215 defines a generally diamond-shaped configuration suitable for translation of cutting member 252 therethrough. The diamond-shaped configuration of channel 215 facilitates accurate and consistent translation of complementary-shaped diamond cutting member 252 therethrough.

Figure 8A:
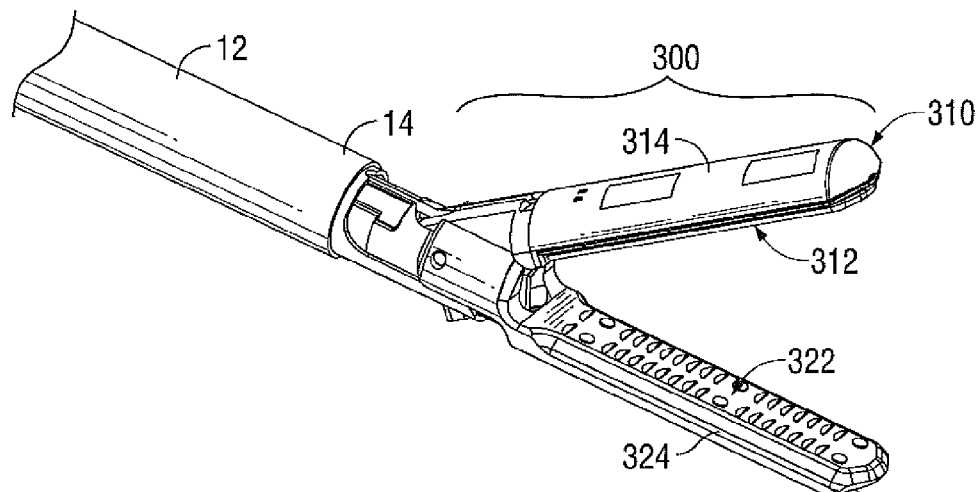
FIG. 8A is an enlarged, perspective view of another embodiment of an end effector assembly for use with the forces of FIG. 1.

Referring now to FIGS. 8A-10B, another end effector assembly for use with forceps 10 is shown generally identified by reference numeral 300. As shown in FIG. 8A, end effector assembly 300 is similar to end effector assembly 100 and includes first and second jaw members 310 and 320. Each jaw member includes an electrically conductive tissue sealing surface 312, 322, respectively, disposed on an opposed surface thereof and a respective outer jaw housing 314, 324. However, end effector assembly 300 is different from end effector assembly 100 in that sealing surfaces 312, 322 of jaw members 310, 320 extend across a substantial area of the opposed surfaces of jaw members 310, 320. In other words, sealing surfaces 312 and 322 do not include channels defined therein.

Figure 8B:
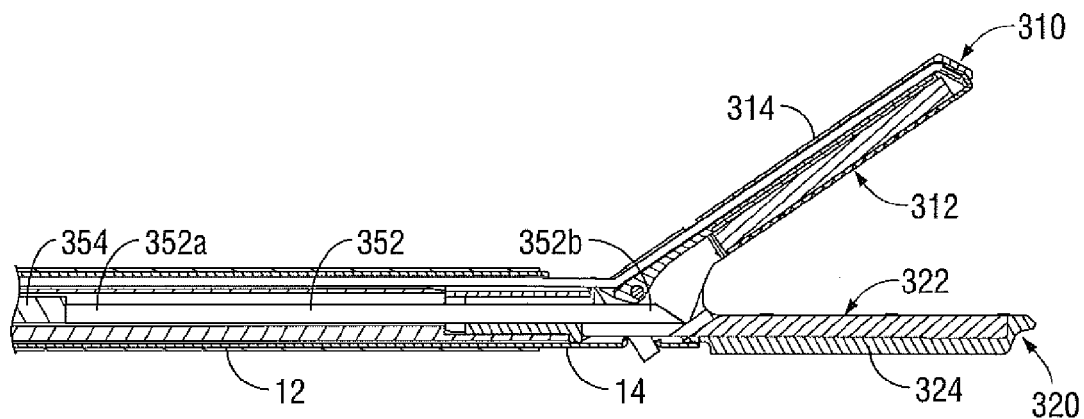
FIG. 8B is a side, cross-sectional view of the end effector assembly of FIG. 8A.

As shown in FIG. 8B, a cutting assembly 350 including a cutting member 352 engaged to a drive bar 354 at a proximal end 352a thereof is disposed within shaft 12 and, as in the previous embodiments, is moveable between a retracted position and an extended position. In the retracted position, cutting member 352 is disposed within shaft 12. Upon activation, e.g., upon depression of trigger 70 (FIG. 1), cutting member 352 is advanced distally from the shaft 12 and between jaw members 310, 320 to cut tissue disposed therebetween.

Figure 9:
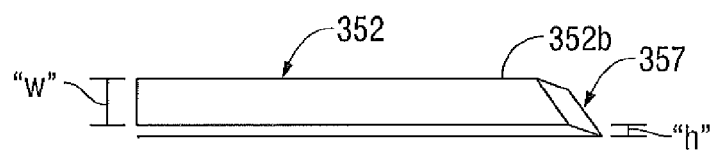
FIG. 9 is a perspective view of another cutting member configured for translation through the end effector assembly of FIG. 8A.

Referring now to FIG. 9, cutting member 352 defines an elongated body having a rectangular front cross-sectional configuration and includes a cutting edge 357 defined at a distal end 352b thereof. More specifically, distal end 352b of cutting member 352 is angled with respect to cutting member 352 to define cutting edge 357. Cutting member 352 defines a width "w" and a height "h." The width "w" may be greater than the height "h" to define the rectangular configuration of cutting member 352. Further, the height "h" of cutting member 352 may be less than a gap distance "g" (FIGS. 10A, 10B) between sealing surfaces 312, 322 when jaw members 310, 320 are in the approximated position. Additionally, the width "w" be less than a width "W" of sealing surfaces 312, 322 of respective jaw members 310, 320.

Figure 10A:
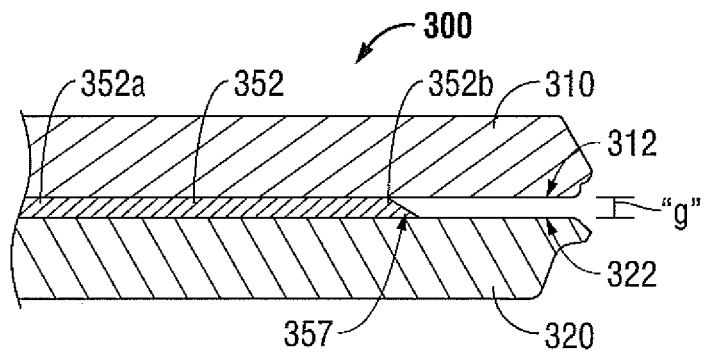
FIG. 10A is a side, cross-sectional view of the end effector assembly of FIG. 8A showing the cutting member of FIG. 9 translating therebetween.
Figure 10B:
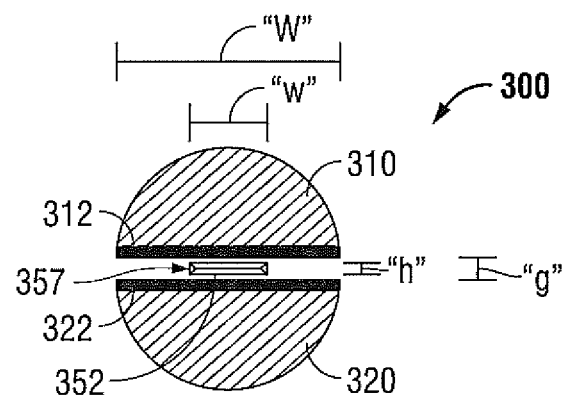
FIG. 10B is a front, cross-sectional view of the end effector assembly of FIG. 8A showing the cutting member of FIG. 9 translating therebetween.
Figure 11:
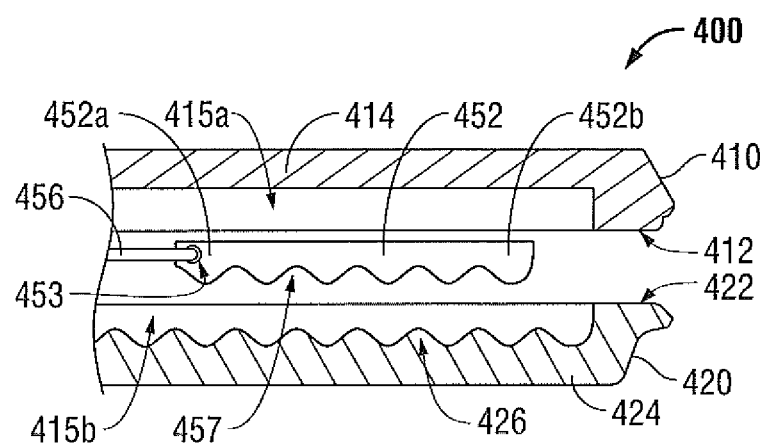
FIG. 11 is a side, cross-sectional view of another end effector assembly according to the present disclosure and configured for use with the forceps of FIG. 1 shown with parts separated.

As shown in FIGS. 10A and 10B, upon deployment of cutting member 352 from the retracted position to the extended position, cutting member 352 is advanced distally between sealing surfaces 312, 322, i.e., through the gap "g," substantially parallel to sealing surfaces 312, 322, to cut tissue disposed therebetween. More particularly, the dimensions of cutting member 352 discussed above permit cutting member 352 to be translated between jaw members 310, 320 without the need for a channel to be defined within jaw members 310 and/or 320 since cutting member 352 is oriented substantially parallel to sealing surfaces 312, 322 of jaw members 310, 320, respectively. In other words, since the height "h" of cutting members 352 is less than the gap distance "g" between jaw members 310, 320 and since the width "w" of cutting member 352 is less than the width "W" of sealing surfaces 312, 322, cutting member 352 may be translated between and parallel to jaw members 310, 320, rather than through a channel defined within jaw members 310, 320, to cut tissue grasped between sealing surfaces 312, 322 of respective jaw members 310, 320. As can be appreciated, design challenges and manufacturing costs are reduced when jaw members 310, 320 and/or sealing surfaces 312, 322 need not include a channel defined therein.

Another embodiment of an end effector assembly, end effector assembly 400, is shown in FIGS. 11-13B and is configured for use with forceps 10 (FIG. 1). End effector assembly 400 includes first and second jaw members 410, 420 that are pivotable with respect to one another between a spaced-apart position and an approximated position for grasping tissue therebetween. Jaw member 410 and/or jaw member 420 each may include an electrically conductive tissue sealing surface 412, 422, respectively, disposed on an opposed surface thereof. Each jaw member 410, 420 also includes a respective outer jaw housing 414, 424.

Jaw members 410, 420 include respective channels 415a, 415b defined therein and extending longitudinally therealong, although one jaw member, e.g., jaw member 420, may include a channel 415b defined therein. Channels 415a, 415b are configured to permit reciprocation of a cutting member 452 therethrough. Channel 415b of jaw member 420 includes a repeating wave-shaped bottom surface, e.g. a sine wave-shaped bottom surface 426. Although sine wave-shaped bottom surface 426 is shown defined within jaw member 420, it is also contemplated that the configuration be switched, i.e., that the repeating wave-shaped bottom surface 426 be defined within channel 415a of jaw member 410.

End effector assembly 400 further includes a cutting assembly 450 (FIGS. 12A and 13A) including a cutting member 452 engaged at a proximal end 452a thereof to a drive bar 454 that is ultimately coupled to a control member, e.g., trigger 70 (FIG. 1), for selectively translating cutting member 452 longitudinally through channels 415a, 415b. As cutting member 452 is translated through channels 415a, 415b, cutting member 452 is vertically displaced between a first position and a second position with respect to channels 415a, 415b, as will be described in greater detail below. Drive bar 454 may be engaged to cutting member 452 through an aperture 453 defined within proximal end 452a of cutting member 452, or may be engaged thereto in any other suitable fashion.

As mentioned above, and with reference now to FIGS. 12A-13B, cutting member 452 is longitudinally translatable from a proximal end 428 of channel 415b to a distal end 429 of channel 415b to cut tissue disposed between jaw members 410, 420 when jaw members 410, 420 are in the approximated position. Cutting member 452 includes a bottom surface 457 defining a sine wave configuration that is shaped complementarily, i.e., has a similar amplitude and wavelength, to the sine wave-shaped bottom surface 426 of channel 415b of jaw member 420. Bottom surface 457 of cutting member 452 is configured as a cutting edge 457, for cutting tissue during translation of cutting member 452 through tissue, as will be described below.

Figure 12A:
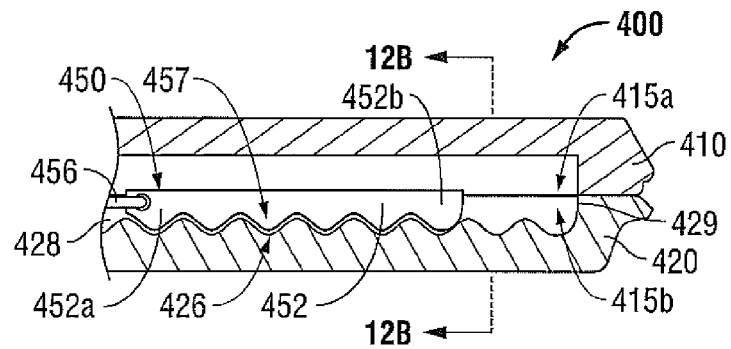
FIG. 12A is a side, cross-sectional view of the end effector assembly of FIG. 11 showing a cutting member in a first position.
Figure 12B:
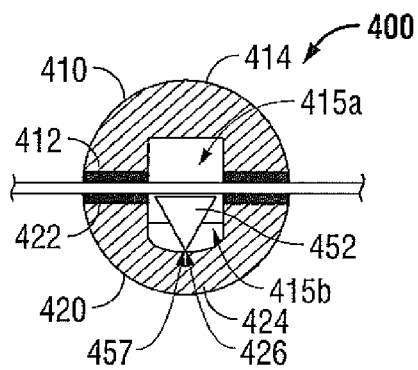
FIG. 12B is a front, cross-sectional view of the end effector assembly of FIG. 11 taken along section line 12B-12B in FIG. 12A.
Figure 13A:
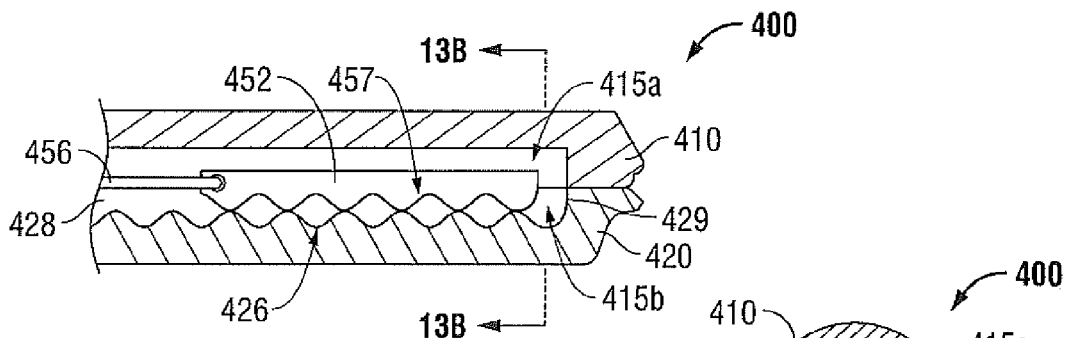
FIG. 13A is a side, cross-sectional view of the end effector assembly of FIG. 11 showing the cutting member in a second position.

Initially, as shown in FIGS. 12A and 12B, cutting member 452 is positioned at proximal end 428 of channel 415b of jaw member 420 in a first position. In this first position, cutting member 452 is out of phase with bottom surface 426 of channel 415b. In other words, sine wave-shaped bottom cutting surface 457 of cutting member 452 is offset from sine wave-shaped bottom surface 426 of channel 415b such that cutting member 452 and channel 415b are substantially mating with one another. More specifically, in this first position, the peaks of sine wave-shaped bottom cutting surface 457 of cutting member 452 are aligned with the valleys of sine wave-shaped bottom surface 426 of channel 415b, and visa-versa such that cutting member 452 is fully disposed within channel 415b, as best shown in FIG. 13A. As can be appreciated, in this first position, bottom cutting surface 457 of cutting member 452 is unexposed.

Figure 13B:
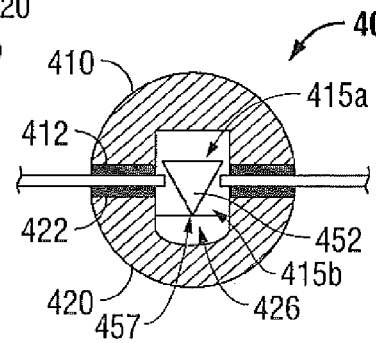
FIG. 13B is a front, cross-sectional view of the end effector assembly of FIG. 11 taken along section line 13B-13B in FIG. 13A.

Upon actuation, e.g., upon depression of trigger 70 (FIG. 1), drive bar 454 urges cutting member 452 distally through channel 415b and, accordingly, cutting member 452 is moved from the first position shown in FIGS. 12A and 12B to the second position shown in FIGS. 13A and 13B. More particularly, as cutting member 452 is translated distally within channel 415b, cutting member 452 is slid along and moved into phase with channel 415b, i.e., cutting member 452 is moved to the second position, such that the peaks of sine wave-shaped bottom cutting surface 457 of cutting member 452 are aligned with the peaks of sine wave-shaped bottom surface 426 of channel 415b and such that the valleys of bottom surface 457 of cutting member 452 are aligned with the valleys of bottom surface 426 of channel 415b. Thus, in this second position, cutting member 452 is vertically displaced from channel 415b. As cutting member 452 is displaced from channel 415b, bottom cutting surface 457 of cutting member 452 is exposed, e.g., bottom cutting surface 457 is extended from channel 415b, to cut tissue disposed between jaw members 410, 420, as best shown in FIGS. 13A and 13B.

During translation of cutting member 452 from proximal end 428 of channel 415b to distal end 429 of channel 415b, cutting member 452 is repeatedly displaced between the first position and the second position as the complementary shaped surfaces (bottom surface 426 of channel 415b and bottom cutting surface 457 of cutting member 452) are moved into and out-of phase with one another. In other words, as cutting member 452 is translated and vertically displaced between the first and second positions, bottom cutting surface 457 of cutting member 452 is exposed such that cutting member 452 is advanced through tissue in a saw-like fashion to dissect tissue disposed between jaw members 410, 420.

Cutting member 452 may be biased toward proximal end 428 of channel 415b, wherein cutting member 452 is in the first position. In such an embodiment, upon translation of cutting member 452 to distal end 429 of channel 415b of jaw member 420, cutting member 452 would be returned under the bias to the first position at proximal end 428 of channel 415b.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:
1. A forceps, comprising:
a housing having a shaft attached thereto and an end effector assembly disposed at a distal end of the shaft, the shaft defining a longitudinal axis, the end effector assembly including:
first and second jaw members disposed in opposed relation relative to one another, at least one of the jaw members moveable with respect to the other between a spaced-apart position and an approximated position for grasping tissue therebetween, the first and second jaw members rotatable about the longitudinal axis and relative to the shaft through a plurality of rotational positions; and
a cutting assembly including a cutting member rotationally fixed with respect to the shaft, the cutting member including at least one cutting edge, the cutting member disposed within the shaft and longitudinally translatable between a retracted position, wherein the cutting member is disposed proximally of the first and second jaw members, and an extended position, wherein the cutting member extends at least partially between the jaw members to cut tissue grasped between the jaw members, the cutting member configured for translation between the retracted and extended positions at each of the plurality of rotational positions of the jaw members with respect to the shaft.
2. The forceps according to claim 1, wherein the cutting member includes a plurality of cutting edges symmetrically disposed about the cutting member and extending longitudinally therealong.

3. The forceps according to claim 1, wherein the cutting member includes a conically-shaped distal end, the conically-shaped distal end extending distally and radially inwardly to form a distal tip of the cutting member.

4. The forceps according to claim 1, wherein a channel is defined within and extends longitudinally along at least one of the jaw members, the channel configured for translation of the cutting member therethrough at each of the plurality of rotational positions of the jaw members with respect to the shaft.

5. The forceps according to claim 1, further comprising a rotating assembly disposed within the housing and operably coupled to the end effector assembly, the rotating assembly selectively rotatable for rotating the end effector assembly with respect to the shaft.

6. The forceps according to claim 1, wherein the cutting member defines a starburst-shaped cross-sectional configuration.

7. The forceps according to claim 4, wherein the channel is shaped at least partially complementary to the cutting member.

* * * * *